United States Patent
Campbell

(10) Patent No.: US 8,750,978 B2
(45) Date of Patent: Jun. 10, 2014

(54) SYSTEM AND SENSOR FOR EARLY DETECTION OF SHOCK OR PERFUSION FAILURE AND TECHNIQUE FOR USING THE SAME

(75) Inventor: Shannon E. Campbell, Boulder, CO (US)

(73) Assignee: Covidien LP, Mansfield, MA (US)

(*) Notice: Subject to any disclaimer, the term of this patent is extended or adjusted under 35 U.S.C. 154(b) by 1181 days.

(21) Appl. No.: 12/338,797

(22) Filed: Dec. 18, 2008

(65) Prior Publication Data

US 2009/0171237 A1 Jul. 2, 2009

Related U.S. Application Data

(60) Provisional application No. 61/009,736, filed on Dec. 31, 2007.

(51) Int. Cl.
  *A61B 5/05* (2006.01)
(52) U.S. Cl.
  USPC ...................................................... 600/547
(58) Field of Classification Search
  USPC ......... 600/547, 300, 554, 593, 529, 538, 485, 600/482, 363; 424/439, 434; 607/134
  See application file for complete search history.

(56) References Cited

U.S. PATENT DOCUMENTS

| | | |
|---|---|---|
| 2,927,584 A | 3/1960 | Wallace |
| 3,769,983 A | 11/1973 | Merav |
| 3,810,474 A | 5/1974 | Cross |
| 3,822,238 A | 7/1974 | Blair et al. |
| 3,913,565 A | 10/1975 | Kawahara |
| 3,971,385 A | 7/1976 | Corbett |
| 3,975,350 A | 8/1976 | Hudgin et al. |
| 3,995,643 A | 12/1976 | Merav |
| 4,022,217 A | 5/1977 | Rowean |
| 4,130,617 A | 12/1978 | Wallace |
| 4,230,108 A | 10/1980 | Young |
| 4,231,365 A | 11/1980 | Scarberry |
| 4,235,239 A | 11/1980 | Elam |
| 4,340,046 A | 7/1982 | Cox |
| 4,569,344 A | 2/1986 | Palmer |
| 4,638,539 A | 1/1987 | Palmer |
| 4,649,913 A | 3/1987 | Watson |

(Continued)

FOREIGN PATENT DOCUMENTS

| | | |
|---|---|---|
| WO | WO 95/05416 | 2/1995 |
| WO | WO 98/15223 | 4/1998 |
| WO | WO 99/16346 | 4/1999 |
| WO | WO 2006/094513 | 9/2006 |

OTHER PUBLICATIONS

Ollmar et al, Diagnostic Potential of Electrical Bio-Impedance for Skin and Oral Mucosa, 2nd International Conference on Biomagnetism, Feb. 1998, pp. 73-74.*

(Continued)

*Primary Examiner* — Brian Szmal
(74) *Attorney, Agent, or Firm* — Fletcher Yoder PC

(57) ABSTRACT

According to various embodiments, a system, method, and sensor are provided that is capable of monitoring electrical impedance of oral or nasal mucosal tissue. Such sensors may be appropriate for assessing gut hypoperfusion, gut ischemia, or the onset of shock. The electrical impedance of the oral mucosa or other tissues in the upper respiratory tract may be used to non-invasively assess the clinical state of gastrointestinal tissue.

12 Claims, 4 Drawing Sheets

(56) References Cited

U.S. PATENT DOCUMENTS

| | | | |
|---|---|---|---|
| 4,696,296 A | 9/1987 | Palmer | |
| 4,700,700 A | 10/1987 | Eliachar | |
| 4,791,920 A | 12/1988 | Fauza | |
| 4,825,859 A | 5/1989 | Lambert | |
| 4,825,861 A | 5/1989 | Koss | |
| 4,834,726 A | 5/1989 | Lambert | |
| 4,836,199 A | 6/1989 | Palmer | |
| 4,838,255 A | 6/1989 | Lambert | |
| 4,850,348 A | 7/1989 | Pell et al. | |
| 4,867,153 A | 9/1989 | Lorenzen et al. | |
| 4,872,579 A | 10/1989 | Palmer | |
| 4,886,059 A | 12/1989 | Weber | |
| 4,927,412 A | 5/1990 | Menasche | |
| 4,938,741 A | 7/1990 | Lambert | |
| 4,963,313 A | 10/1990 | Noddin et al. | |
| 4,967,743 A | 11/1990 | Lambert | |
| 4,979,505 A | 12/1990 | Cox | |
| 5,020,534 A | 6/1991 | Pell et al. | |
| 5,021,045 A | 6/1991 | Buckberg et al. | |
| 5,025,806 A | 6/1991 | Palmer et al. | |
| 5,029,580 A | 7/1991 | Radford et al. | |
| 5,033,466 A | 7/1991 | Weymuller, Jr. | |
| 5,060,646 A | 10/1991 | Page | |
| 5,065,754 A | 11/1991 | Jensen | |
| 5,074,840 A | 12/1991 | Yoon | |
| 5,076,268 A | 12/1991 | Weber | |
| 5,098,379 A | 3/1992 | Conway et al. | |
| 5,103,816 A | 4/1992 | Kirschbaum et al. | |
| 5,107,829 A | 4/1992 | Lambert | |
| 5,120,322 A | 6/1992 | Davis et al. | |
| 5,122,122 A | 6/1992 | Allgood | |
| 5,133,345 A | 7/1992 | Lambert | |
| 5,135,516 A | 8/1992 | Sahatjian et al. | |
| 5,137,671 A | 8/1992 | Conway et al. | |
| 5,158,569 A | 10/1992 | Strickland et al. | |
| 5,165,420 A | 11/1992 | Strickland | |
| 5,176,638 A | 1/1993 | Don Michael | |
| 5,190,053 A * | 3/1993 | Meer | 607/134 |
| 5,190,810 A | 3/1993 | Kirschbaum et al. | |
| 5,199,427 A | 4/1993 | Strickland | |
| 5,201,310 A | 4/1993 | Turnbull et al. | |
| 5,207,643 A | 5/1993 | Davis | |
| 5,215,522 A | 6/1993 | Page et al. | |
| 5,218,957 A | 6/1993 | Strickland | |
| 5,230,332 A | 7/1993 | Strickland | |
| 5,233,979 A | 8/1993 | Strickland | |
| 5,246,012 A | 9/1993 | Strickland | |
| 5,250,070 A | 10/1993 | Parodi | |
| 5,251,619 A | 10/1993 | Lee | |
| 5,261,896 A | 11/1993 | Conway et al. | |
| 5,263,478 A | 11/1993 | Davis | |
| 5,269,770 A | 12/1993 | Conway et al. | |
| 5,277,177 A | 1/1994 | Page et al. | |
| 5,290,585 A | 3/1994 | Elton | |
| 5,291,887 A | 3/1994 | Stanley et al. | |
| 5,304,121 A | 4/1994 | Sahatjian | |
| 5,331,027 A | 7/1994 | Whitbourne | |
| 5,360,402 A | 11/1994 | Conway et al. | |
| 5,370,656 A | 12/1994 | Shevel | |
| 5,370,899 A | 12/1994 | Conway et al. | |
| 5,374,261 A | 12/1994 | Yoon | |
| 5,392,787 A | 2/1995 | Yoon | |
| 5,397,302 A | 3/1995 | Weaver et al. | |
| 5,407,423 A | 4/1995 | Yoon | |
| 5,417,671 A | 5/1995 | Jackson | |
| 5,423,745 A | 6/1995 | Todd et al. | |
| 5,439,457 A | 8/1995 | Yoon | |
| 5,443,063 A | 8/1995 | Greenberg | |
| 5,447,505 A | 9/1995 | Valentine et al. | |
| 5,451,204 A | 9/1995 | Yoon | |
| 5,466,231 A | 11/1995 | Cercone et al. | |
| 5,469,864 A | 11/1995 | Rosenblatt | |
| 5,482,740 A | 1/1996 | Conway et al. | |
| 5,484,426 A | 1/1996 | Yoon | |
| 5,487,730 A | 1/1996 | Maracadis et al. | |
| 5,494,029 A | 2/1996 | Lane et al. | |
| 5,501,669 A | 3/1996 | Conway et al. | |
| 5,507,284 A | 4/1996 | Daneshvar | |
| 5,509,899 A | 4/1996 | Fan et al. | |
| 5,524,642 A | 6/1996 | Rosenblatt | |
| 5,545,132 A | 8/1996 | Fagan et al. | |
| 5,556,391 A | 9/1996 | Cercone et al. | |
| 5,593,718 A | 1/1997 | Conway et al. | |
| 5,599,292 A | 2/1997 | Yoon | |
| 5,599,299 A | 2/1997 | Weaver et al. | |
| 5,599,321 A | 2/1997 | Conway et al. | |
| 5,611,336 A | 3/1997 | Page et al. | |
| 5,613,950 A | 3/1997 | Yoon | |
| 5,649,902 A | 7/1997 | Yoon | |
| 5,653,229 A | 8/1997 | Greenberg | |
| 5,665,477 A | 9/1997 | Meathrel et al. | |
| 5,670,111 A | 9/1997 | Conway et al. | |
| 5,674,192 A | 10/1997 | Sahatjian et al. | |
| 5,693,014 A | 12/1997 | Abele et al. | |
| 5,694,922 A | 12/1997 | Palmer | |
| 5,697,365 A | 12/1997 | Pell | |
| 5,700,239 A | 12/1997 | Yoon | |
| 5,715,815 A | 2/1998 | Lorenzen et al. | |
| 5,720,726 A | 2/1998 | Marcadis et al. | |
| 5,722,931 A | 3/1998 | Heaven | |
| 5,730,123 A | 3/1998 | Lorenzen | |
| 5,733,252 A | 3/1998 | Yoon | |
| 5,735,271 A | 4/1998 | Lorenzen et al. | |
| 5,765,559 A | 6/1998 | Kim | |
| 5,769,882 A | 6/1998 | Fogarty et al. | |
| 5,810,786 A | 9/1998 | Jackson et al. | |
| 5,819,733 A | 10/1998 | Bertram | |
| 5,827,215 A | 10/1998 | Yoon | |
| 5,843,017 A | 12/1998 | Yoon | |
| 5,843,028 A | 12/1998 | Weaver et al. | |
| 5,843,060 A | 12/1998 | Cercone | |
| 5,843,089 A | 12/1998 | Sahatjian et al. | |
| 5,868,719 A | 2/1999 | Tsukernik | |
| 5,908,406 A | 6/1999 | Ostapchenko | |
| 5,951,597 A | 9/1999 | Westlund et al. | |
| 5,954,706 A | 9/1999 | Sahatjian | |
| 5,954,740 A | 9/1999 | Ravenscroft et al. | |
| 5,971,954 A | 10/1999 | Conway et al. | |
| 5,976,072 A | 11/1999 | Greenberg | |
| 5,997,503 A | 12/1999 | Willis et al. | |
| 5,997,546 A | 12/1999 | Foster et al. | |
| 6,010,480 A | 1/2000 | Abele et al. | |
| 6,012,451 A | 1/2000 | Palmer | |
| 6,048,332 A | 4/2000 | Duffy et al. | |
| 6,110,192 A | 8/2000 | Ravenscroft et al. | |
| 6,129,547 A | 10/2000 | Cise | |
| 6,152,136 A | 11/2000 | Pagan | |
| 6,169,123 B1 | 1/2001 | Cercone | |
| 6,210,364 B1 | 4/2001 | Anderson et al. | |
| 6,214,895 B1 | 4/2001 | Cercone | |
| 6,227,200 B1 | 5/2001 | Crump et al. | |
| 6,240,321 B1 | 5/2001 | Janke et al. | |
| 6,248,088 B1 | 6/2001 | Yoon | |
| 6,264,631 B1 | 7/2001 | Willis et al. | |
| 6,264,633 B1 | 7/2001 | Knorig | |
| 6,277,089 B1 | 8/2001 | Yoon | |
| 6,285,897 B1 | 9/2001 | Kilcoyne et al. | |
| 6,312,421 B1 | 11/2001 | Boock | |
| 6,322,586 B1 | 11/2001 | Monroe et al. | |
| 6,364,856 B1 | 4/2002 | Ding et al. | |
| 6,378,521 B1 | 4/2002 | Van Den Berg | |
| 6,394,093 B1 | 5/2002 | Lethi | |
| 6,395,012 B1 | 5/2002 | Yoon et al. | |
| 6,398,266 B1 | 6/2002 | Crump | |
| 6,409,716 B1 | 6/2002 | Sahatjian et al. | |
| 6,470,200 B2 | 10/2002 | Walker et al. | |
| 6,481,436 B1 | 11/2002 | Neame | |
| 6,494,203 B1 | 12/2002 | Palmer | |
| 6,503,231 B1 | 1/2003 | Prausnitz et al. | |
| 6,524,274 B1 | 2/2003 | Rosenthal et al. | |
| 6,526,977 B1 | 3/2003 | Göbel | |
| 6,543,451 B1 | 4/2003 | Crump et al. | |
| 6,551,272 B2 | 4/2003 | Gobel | |
| 6,572,813 B1 | 6/2003 | Zhang et al. | |

(56) References Cited

U.S. PATENT DOCUMENTS

| | | | |
|---|---|---|---|
| 6,576,712 B2 | 6/2003 | Feldstein et al. | |
| 6,584,970 B1 | 7/2003 | Crump et al. | |
| 6,588,425 B2 | 7/2003 | Rouns et al. | |
| 6,588,427 B1 | 7/2003 | Carlsen et al. | |
| 6,602,218 B2 | 8/2003 | Yoon | |
| 6,602,219 B2 | 8/2003 | Madsen et al. | |
| 6,609,520 B1 | 8/2003 | Carlsen et al. | |
| 6,612,304 B1 | 9/2003 | Cise et al. | |
| 6,612,305 B2 | 9/2003 | Fauza | |
| 6,613,025 B1 | 9/2003 | Palasis | |
| 6,615,835 B1 | 9/2003 | Cise et al. | |
| 6,620,128 B1 | 9/2003 | Simhambhatla | |
| 6,623,450 B1 | 9/2003 | Dutta | |
| 6,629,530 B2 | 10/2003 | Cise | |
| 6,632,091 B1 | 10/2003 | Cise et al. | |
| 6,651,664 B1 | 11/2003 | Lomholt | |
| 6,688,306 B1 | 2/2004 | Cise et al. | |
| 6,698,424 B2 | 3/2004 | Madsen et al. | |
| 6,705,320 B1 | 3/2004 | Anderson | |
| 6,722,368 B1 | 4/2004 | Shaikh | |
| 6,726,696 B1 | 4/2004 | Houser et al. | |
| 6,745,773 B1 | 6/2004 | Gobel | |
| 6,767,340 B2 | 7/2004 | Willis et al. | |
| 6,769,430 B1 | 8/2004 | Carlsen et al. | |
| 6,770,066 B1 | 8/2004 | Weaver et al. | |
| 6,786,876 B2 | 9/2004 | Cox | |
| 6,790,221 B2 | 9/2004 | Monroe et al. | |
| 6,796,309 B2 | 9/2004 | Nash et al. | |
| 6,802,317 B2 | 10/2004 | Göbel | |
| 6,805,125 B1 | 10/2004 | Crump et al. | |
| 6,808,521 B1 | 10/2004 | McMichael | |
| 6,814,730 B2 | 11/2004 | Li | |
| 6,890,339 B2 | 5/2005 | Sahatjian et al. | |
| 6,908,449 B2 | 6/2005 | Willis et al. | |
| 6,916,307 B2 | 7/2005 | Willis et al. | |
| 6,923,786 B2 | 8/2005 | Rouns et al. | |
| 6,997,909 B2 | 2/2006 | Goldberg | |
| 7,040,321 B2 | 5/2006 | Gobel | |
| 7,040,322 B2 | 5/2006 | Fortuna | |
| 7,066,905 B2 | 6/2006 | Squire et al. | |
| 7,147,252 B2 | 12/2006 | Teuscher et al. | |
| 7,258,120 B2 | 8/2007 | Carlsen et al. | |
| 7,618,376 B2* | 11/2009 | Kimball | 600/485 |
| 2002/0032407 A1 | 3/2002 | Willis et al. | |
| 2002/0082552 A1 | 6/2002 | Ding et al. | |
| 2002/0195110 A1 | 12/2002 | Watton | |
| 2003/0116162 A1 | 6/2003 | Madsen et al. | |
| 2003/0225369 A1 | 12/2003 | McMichael et al. | |
| 2003/0225392 A1 | 12/2003 | McMichael et al. | |
| 2003/0225393 A1 | 12/2003 | McMichael et al. | |
| 2004/0079376 A1 | 4/2004 | Melker | |
| 2004/0106899 A1 | 6/2004 | McMichael et al. | |
| 2004/0106900 A1 | 6/2004 | Triebes et al. | |
| 2004/0106901 A1 | 6/2004 | Letson et al. | |
| 2004/0116819 A1* | 6/2004 | Alt | 600/547 |
| 2004/0116898 A1 | 6/2004 | Hawk | |
| 2004/0154623 A1 | 8/2004 | Schaeffer et al. | |
| 2004/0193100 A1 | 9/2004 | Van Hooser et al. | |
| 2004/0193101 A1 | 9/2004 | Van Hooser et al. | |
| 2004/0215142 A1 | 10/2004 | Matheis et al. | |
| 2004/0221853 A1 | 11/2004 | Miller | |
| 2004/0255951 A1 | 12/2004 | Grey | |
| 2005/0004560 A1 | 1/2005 | Cox | |
| 2005/0033267 A1 | 2/2005 | Decaria | |
| 2005/0033268 A1 | 2/2005 | Decaria | |
| 2005/0033269 A1 | 2/2005 | Decaria | |
| 2005/0038381 A1 | 2/2005 | McMichael | |
| 2005/0054939 A1* | 3/2005 | Ben-Ari et al. | 600/547 |
| 2005/0065468 A1 | 3/2005 | Goebel | |
| 2005/0124932 A1 | 6/2005 | Foster et al. | |
| 2005/0124935 A1 | 6/2005 | McMichael | |
| 2005/0137619 A1 | 6/2005 | Schewe et al. | |
| 2005/0166924 A1 | 8/2005 | Thomas et al. | |
| 2005/0215918 A1* | 9/2005 | Frantz et al. | 600/547 |
| 2007/0078318 A1 | 4/2007 | Kling et al. | |
| 2007/0295336 A1 | 12/2007 | Nelson | |
| 2007/0295337 A1 | 12/2007 | Nelson | |
| 2007/0296125 A1 | 12/2007 | Colburn et al. | |
| 2008/0000482 A1 | 1/2008 | Maguire et al. | |
| 2008/0039700 A1* | 2/2008 | Drinan et al. | 600/301 |
| 2008/0305149 A1* | 12/2008 | Hirt et al. | 424/434 |
| 2009/0232872 A1* | 9/2009 | Davidson et al. | 424/439 |

OTHER PUBLICATIONS

Gonzalez et al, Classification of Impedance Spectra for Monitoring Ischemic Injury in the Gastric Mucosa in a Septic Shock Model in Pigs, Proceedings of the 25th Annual International Conference of the IEEE EMBS, Sep. 17-21, 2003, pp. 2269-2272.*

Weisner et al, CT of Acute Bowel Ischemia, Radiology 2003, 226:635-650.*

Nakagawa et al, Sublingual Capnometry for Diagnosis and Quantitation of Circulatory Shock, Am J Respir Crit Care Med, 1998; 157:1838-1843.*

Tecogel brochure page, Noveon Thermedics Polymer Products, Oct. 2003.

Ayşe Gönen Karakeçiliet al.; "Comparison of Bacterial and Tissue Cell Initial Adhesion on Hydrophilic/Hydrophobic Biomaterials," J Biomater. Sci. Polymer Edn, vol. 13, No. 2, pp. 185-196 (2002).

Shintani; "Modification of Medical Device Surface to Attain Anti-Infection," National Institute of Health Sciences; Trends Biomater. Artif. Organs, vol. 18(1), pp. 1-8 (2004).

College of Pharmacy, Oregon State University and 3M Drug Delivery Systems; 3M Study Provides First Direct Comparison of Oral Controlled Release, Transdermal and Transmucosal Drug Delivery in Humans; article; pp. 10-12.

Pharmaceutical Polymers; Bulletin 16; entitled "Biodhesion"; 18 pages.

Michael J Rathbone et al.; entitled "Modified-Release Drug Delivery Technology"; web page http://www.chipsbooks.com/modrug.htm; printed Sep. 28, 2004; 3 pages.

Article entitled "STRIANT (testosterone buccal system) mucoadhesive"; web page http://www.columbialabs.com/Striant/Striant_Full_Prescribing_info.htm; printed Oct. 6, 2004; 5 pages.

Ingenta: article summary entitled Mucoadhesive and Penetration Enhancement Properties of Three Grades of Hyaluronic Acid Using Porcine Buccal and Vaginal Tissue, Caco-2 Cell Lines, a Rat Jejunum; Journal of Pharmacy and Pharmacology; Sep. 1, 2004; vol. 56, No. 9, 1083-1090(8); from webpage http://www.ingenta.com/isis/searching/Expand/ingenta?pub=infobike;//rpsgb/jpp/2004/000 . . . on Oct. 6, 2004; 1 page.

Web article; entitled Opportunities, Mucoadhesive Erodible Disc (OraDisc); Pharmalicensing.com; http://pharmalicensing.com/licensing/displicopp/2316 printed on Sep. 28, 2004; 2 pages.

Nicholas A. Peppas; article entitled Nanoscale Technology of Mucoadhesive Interactions; Advanced Drug Delivery Reviews 56 (2004) 1675-1687; 13 pages.

Sartomer Application Bulletin; "Functional Acrylic Monomers as Modifiers for PVC Plastisol Formulations,"; pp. 1-6.

Lev Bromberg; article entitled Biadhesive properties and rheology of polyether-modified poly(acrylic acid) hydrogels; Elsevier; international journal of pharmaceutics; 16 pages.

Sanju Dhawan; article entitled: "Evaluation of Mucoadhesive Properties of Chitosan Microspheres Prepared by Different Methods"; web page http://www.aapspharmscitch.org/view.asp?art=pt050467&pdf=yes; 13 pages.

Juan Manuel Llabot; article entitled: "Double-Layered Mucoadhesive Tablets Containing Nystatin"; Submitted: Mar. 11, 2002; AAPS PharmSciTech 2002; 3 (3) article 22 (http://www.aapspharmsci.org) 6 pages.

Edith Mathiowitz et al.; article entitled "Bioadhesive Drug Delivery Systems: Fundamentals, Novel Approaches and Development"; website http://www.chipsbooks.com/bioadhes.htm; printed out on Sep. 28, 2004; 3 pages.

Sanju Dhawan; article entitled Evaluation of Mucoadhesive Properties of Chitosan Microspheres Prepared by Different Methods; Submitted: May 17, 2004; AAPS PharmSciTech 2004; 5 (4) Article 57 (http://www.aapspharmscitech.org). 7 pages.

(56) References Cited

OTHER PUBLICATIONS

Article entitled "A comparison of TMD Matrix and Reservoir Configurations"; 1 page.
Webpage article entitled "Columbia Laboratories, Inc."; http://www.columbialabs.com/AboutUs.htm; 1 page.
Website article entitled "Our Bioadhesive Gel"; http:www.prochieve8.com/bioadhesive/default.aspx; 2 pages.
Website article entitled "Technology Portfolio"; http://www.accesspharma.com/products/index.html; 10 pages.
Website article entitled STRIANT (Testosterone Buccal System) Mucoadhesive CIII; http;//www.columbialabs.com/Striant/Striant_Fact_Sheet.html; 3 pages.
Drug insert pamplet for STRIANT (testosterone buccal system) 2 pages.
Doglio GR et al., "Gastric Mucosal pH as a Prognostic index of mortality in critically ill patients". Crit Care Med 19: 1037-1040, 1991.
Fiddian-Green RG, et al., "Back-diffusion of CO2 and its influence on the intramural pH in gastric mucosa". J Surg Res 33: 39-48, 1982.
Weil MH, et al.; "Sublingual capnometry: a new noninvasive measurement for diagnosis and quantitation of severity of circulatory shock". Crit Care Med 27: 1225-1229, 1999.

Peppas, Nikolaos A. et al., "Hydrogels as mucoadhesive and bioadhesive materials: a review," *Biomaterials*, 1996, pp. 1553-1561, vol. 17, No. 16.
Klainer, Albert S., M.D. et al., "Surface Alterations Due to Endotracheal Intubation," *The American Journal of Medicine*, May 1975, pp. 674-683, vol. 58.
MacCabee, Mendy S., M.D. et al., "Paranasal Sinus Mucosal Regeneration: The Effect of Topical Retinoic Acid," *American Journal of Rhinology*, 2003, pp. 133-137, vol. 17.
Shoemaker, W.C. et al.; "Noninvasive Hemodynamic Monitoring of Critical Patients in the Emergency Department"; http://www.ncbi.nlm.nih.gov/entrez/query.
Gonzalez, Cesar A., et al.; "Impedance Spectroscopy for Monitoring Ischemic Injury in the Intestinal Mucosa"; 2003 IOP Publishing Ltd., pp. 277-289, (2003).
Tamura, T. et al.; "Modelling of the Dielectric Properties of Normal and Irradiated Skin"; 1994 IOP Publishing Ltd., pp. 927-936.
Sato, Yoji et al.; "Esophageal $PCO_2$ as a Monitor of Perfusion Failure During Hemorrhagic Shock"; 1997 of the American Physiological Society, pp. 558-562.
Gonzalez-Correa, C.A. et al.; "Electrical Bioimpedance Readings Increase with Higher Pressure Applied to the Measuring Probe"; 2005 IOP Publishing Ltd., pp. S39-S47.

* cited by examiner

SYSTEM AND SENSOR FOR EARLY DETECTION OF SHOCK OR PERFUSION FAILURE AND TECHNIQUE FOR USING THE SAME

RELATED APPLICATION

This application claims priority from U.S. Patent Application No. 61/009,736 which was filed Dec. 31, 2007 and is incorporated herein by reference in its entirety.

BACKGROUND

The present disclosure relates generally to medical devices and, more particularly, to a sensor placed on a mucosal tissue used for measuring physiological parameters of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

In some instances, physicians may wish to have information about the clinical state of tissues that are not easily accessible, such as gastrointestinal tissue. For example, clinicians may wish to assess certain parameters of gastrointestinal tissue to determine whether a patient is in shock. Shock is a clinical syndrome characterized by decreased blood flow to the capillary beds. This condition typically occurs when arterial pressure and subsequently tissue blood flow decrease to a degree that the amount of delivered oxygen is inadequate to meet the metabolic needs of the tissue. During shock, the body directs blood to the heart and the brain, often at the expense of relatively less important organs such as the liver, skin, muscle, and gut. Prolonged shock may result in ischemia in tissues that have experienced diminished blood flow for a sufficient length of time. Ischemia in the gut may disrupt the normal intestinal barrier function, resulting in gut-derived bacteria and their endotoxins being able to move from the gut into other organs via the blood. This, in turn, may lead to toxemia or sepsis. Therefore, early detection of gut tissue damage may prevent the onset of shock or organ failure.

As prolonged gut hypoperfusion typically precedes gut ischemia, early detection of perfusion failure in the gut may prevent widespread tissue damage and may also reduce the incidence of toxemia or sepsis. Accordingly, physicians have developed methods for assessing hypoperfusion in the gut. However, these methods are associated with certain disadvantages. For example, assessing the hypoperfusion of gastrointestinal tissue by impedance spectroscopy may provide clinical information regarding shock, mucosal perfusion, or ischemia. This procedure involves insertion of an intestinal catheter, which is labor-intensive for a clinician to perform and uncomfortable for patients. An alternative technique uses an ion-sensitive field-effect transistor (ISFET) sensor to detect $PCO_2$ in the gastric wall, which also correlates to the onset of shock. However, this technique is also invasive and involves direct contact with the gut.

Accordingly, a reliable, noninvasive monitor for gut perfusion failure may improve the diagnosis and management of patients with gut ischemia.

SUMMARY

Certain aspects commensurate in scope with the disclosure are set forth below. It should be understood that these aspects are presented merely to provide the reader with a brief summary of certain forms the disclosure might take and that these aspects are not intended to limit the scope of the disclosure. Indeed, the disclosure may encompass a variety of aspects that may not be set forth below.

There is provided a diagnostic physiological monitoring system that includes a first electrode capable of applying a current to an oral or nasal mucosa of a patient; a second electrode capable of detecting the applied current from the mucosa and output a value related to electrical impedance of the mucosa; and a monitor operatively coupled to the first electrode and the second electrode, wherein the monitor is capable of receiving the impedance value and performing an operation on the impedance value to determine a gastrointestinal tissue condition of the patient.

There is also provided a method that includes receiving an impedance measurement from at least two electrodes attached to an oral or nasal mucosa and analyzing the impedance measurement to determine a clinical condition including at least one of gut hypoperfusion, gut ischemia, shock, or organ failure.

There is also provided a method of asserting a shock treatment protocol, including attaching at least two electrodes to an oral or nasal mucosa, wherein the electrodes are configured to transmit an impedance measurement to a monitor that is operatively coupled to the electrodes; observing an alarm on the monitor, wherein the alarm is configured to indicate a shock condition by analyzing the impedance measurement; and proceeding with a shock treatment protocol.

There is also provided a sensor configured to detect gut ischemia that includes a first electrode capable of applying a current to an oral or nasal mucosa, a second electrode capable of detecting the applied current and output a value related to the impedance of the mucosa, a nonconductive sheet adapted to space the first electrodes and the second electrode at a generally fixed distance relative to one another, and a mucoadhesive layer disposed on a mucosal tissue-contacting side of the first electrode and the second electrode.

BRIEF DESCRIPTION OF THE DRAWINGS

Advantages of the disclosure may become apparent upon reading the following detailed description and upon reference to the drawings in which.

DETAILED DESCRIPTION

Figure 1:
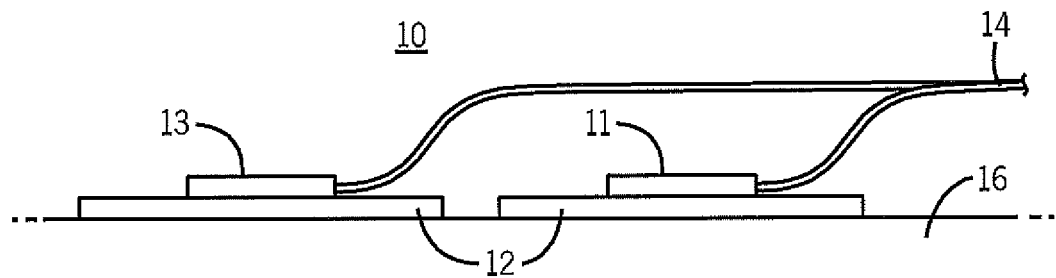
FIG. 1 is a side view of an electrical impedance sensor showing a mucoadhesive layer attached to mucosal tissue according to an embodiment.

One or more embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions may be made to achieve the developers' specific goals, for example compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

According to various embodiments ensors and monitoring systems are provided herein that may detect gut ischemia by monitoring the electrical impedance of oral and/or nasal mucosal tissue. The electrical impedance of oral or nasal mucosal tissue may serve as an indicator of several gastrointestinal tissue conditions including gut ischemia, gut injury, gut hypoperfusion. Additionally, such sensors may be useful for predicting the onset of shock or organ failure. Generally, monitoring occurs while an electrical impedance sensor is secured to oral or nasal mucosal tissue, for example with a mucoadhesive. A sensor may be attached to any oral or nasal mucosal tissue that may be easily accessible to a healthcare worker, for example, buccal or sublingual tissue.

Generally, it is envisioned that electrical impedance sensors according to various embodiments may be appropriate for use in determining the electric impedance level in mucosal tissues. Electrical resistance of the mucosal tissue reflects the conducting properties of electrolytes and other components within the tissue, and the overall impedance reflects the interaction of these components within a complex tissue structure. As a result, electrical properties in tissue exhibit change as ischemia or perfusion failure occurs in the area. In the case of perfusion failure of internal organs, mucosal tissue in the gut and esophagus exhibit these changes as the condition advances. For example, as ischemic injury progresses, inflammatory mediators affect the membrane permeability of various cells within the gastrointestinal tissue. As a result, the balance of intracellular volume and extracellular volume changes as ischemia develops. The disruption of cell membrane permeability also affects cell transport and cell death. Each of these changes causes a shift in the electrical properties of the cells, and in turn the tissue, that may be assessed by measuring the electrical impedance of the tissue. Because the tissue of the gut is physically linked to the mucosal tissue of the upper gastrointestinal tract, hypoperfusion of the gut results in a corresponding reduction in blood flow to the mucosal tissue of the mouth and nose. Accordingly, impedance analysis of oral or nasal mucosal tissue may be useful in early detection of gut hypoperfusion.

According to various embodiments, sensors for measuring electrical impedance of mucosal tissue of the upper gastrointestinal tract may include one or more electrodes for measuring electrical impedance. For example, one or more electrodes may be secured inside the cheek or under the tongue. Further, the sensors as described herein are appropriate for use adjacent to or proximate to any mucosal surface, i.e. patient surfaces that include a mucous membrane or surfaces that are associated with mucus production. In addition to the oral mucosa, mucosal surfaces may include anal, respiratory (i.e. nasal) or urogenital surfaces. Additionally, oral or nasal mucosal impedance measurements may be part of a larger patient monitoring strategy that includes monitoring of health rate, blood pressure and/or blood oxygen saturation.

Electrical impedance sensors in accordance with the present disclosure may include one electrode for applying an electrical current and one electrode for detecting the voltage drop of the applied current as a result of the impedance of the tissue. In one embodiment, at least one current source electrode sends a small, high frequency sinusoidal current through the tissue. At least one detecting electrode measures the resulting voltage drop and phase lag of the sinusoidal current that has passed through the tissue. The electrodes may be disposable or reusable. In addition, the electrodes may be appropriate for short-term (e.g. minutes) or long-term (e.g. hours, days, or longer) monitoring. The electrodes may also be of various sizes or types depending upon the patient, measurement period, and other specifications. Generally, the impedance sensor includes at least one current sourcing electrode and at least one voltage detecting electrode. It should be noted that, in one embodiment, it may be appropriate to use an array of current source electrodes and detecting electrodes.

Turning now to the drawings, and referring to an embodiment in FIG. 1, sensor 10 is shown that includes current source electrodes 11 and voltage detection electrode 13, with a mucoadhesive layer 12 on the skin contacting surface of the electrode. Not pictured is a monitoring device, which may be connected to sensor 10 by lead 14. In the present embodiment, the mucoadhesive layer 12 affixes the sensor 10 to the oral mucosal tissue 16 of the patient. Components of sensor 10 and lead 14 may be made of any suitable material that may be generally suited to the aqueous environment of the mucous membrane, for example plastic. In other embodiments (not shown), it may be advantageous to package the electrodes in foil or other protective materials in order to protect the mucoadhesive layer 12 prior to use and to prevent drying out or oxidation of the mucoadhesive layer 12.

The electrodes 11 and 13 may be of any suitable type for bioimpedance measurements, such as those offered for sale by Biopac Systems, Inc. (Goleta, Calif.). As should be appreciated, conductive gels (not pictured) may be used to enhance the electrical connection between the mucosal skin and the electrode. In an embodiment, a conductive gel may be used in a central area of the body of the electrode and may be surrounded by a mucoadhesive to ensure that the gel does not leak out from the electrode and to ensure that a conductive path to the electrode may be maintained. An alternative embodiment may include a gel substance that performs as both a mucoadhesive and a conductive gel.

In an embodiment, the sensor 10 may be secured to the oral or nasal mucosal tissue with a mucoadhesive or other suitable mounting device, such as a clip. The mucoadhesive layer may be applied to a flexible fabric or plastic non-conductive sheet which may be the portion of the electrode that may directly contact the mucosal surface. A secure mounting of the sensor to oral or nasal mucosal tissue with mucoadhesives reduces movement of the sensor, which may cause signal artifacts. Use of a mucoadhesive also prevents fluids or other substances from interfering with the sensor measurement while securing the sensor to the mucous tissue. The term mucoadhesive refers to a substance that sticks to or adheres to the mucous membrane by any number of mechanisms, for example, but not limited to the following: hydrogen-bonding, ionic interaction, hydrophobic interaction, van der Waals interaction, or combinations thereof.

In an embodiment, the mucoadhesive layer 12 may include a variety of mucoadhesive compositions to secure electrodes to mucosal tissue according to the present disclosure. As one of ordinary skill in the art may recognize, a mucoadhesive substance may be chosen that allows electrical signals to be conducted and received from the mucosal tissue to the electrodes. Suitable mucoadhesives include, but are not limited to hydroxypropyl cellulose, hydroxypropyl methylcellulose, hydroxyethylcellulose, ethylcellulose, carboxymethylcellulose, dextran, guar gum, polyvinyl pyrrolidone, pectins, starches, gelatin, casein, acrylic acid polymers, polymers of acrylic acid esters, vinyl polymers, vinyl copolymers, polymers of vinyl alcohols, alkoxy polymers, polyethylene oxide polymers, polyethers, and any combination of the above.

In various embodiments, the mucoadhesive may be a biocompatible polymer, for example polyacrylic acid, that may be cross-linked with an acceptable agent to create an insoluble gel. The use of an insoluble gel may be desirable, particularly for long term monitoring, since it remains adhered to the mucosal tissue for relatively long periods of time. Cross-linked polyacrylic acid polymers, for example Noveon and Carbomer, may be appropriate for use for three to five days or longer. Noveon and Carbomer-based polymers are weak acids and contain many negatively-charged carboxyl-groups. The multiple negative charges on these polymers promote hydrogen-bonding between the polymers and the negatively charged mucin, a glycoprotein that mediates attachment of mucus to the epithelial lining. A mucoadhesive polymer may also include acrylic acid polymers (e.g. Carbopol® 940, also known as Carbomer® 940, Carbopol 934P and Carbopol® 980, products of BF Goodrich), methyl vinyl/maleic acid copolymers (e.g. Gantrez® S-97, a product of International Specialty Products), polyvinyl pyrrolidone also known as povidone (e.g. Plasdone® K-90, a product of International Specialty Products). These polymers impart relatively high viscosity at relatively low concentrations. They may be incorporated onto a sensor in amounts ranging from about 0.01% to about 10% by weight relative to the total composition. These viscosity modifying agents further act to improve the film adhesion of the composition to mucous membranes. Carbopol® 980, in one embodiment, may be 2-3% by weight of the total composition.

In an embodiment the mucoadhesive may be formulated as either a liquid or as a gel. If a liquid formulation may be desired, a relatively low concentration (e.g. 0.1-1%) of the mucoadhesive/viscosity modifying agent may be used. If a gel formulation is desired, a higher concentration (e.g. 1.5-4%) of the suitable viscosity modifying/mucoadhesive agent may be incorporated into the polymethacrylate/solvent vehicle for gel formation. The mucoadhesive may further comprise excipients e.g. plasticizers, flavorings, sweeteners and/or colorants. Examples of plasticizers include triethyl citrate, polyethylene glycol and glycerin. Such plasticizers may be present in amounts generally ranging from about 1% to about 10% by weight relative to the total composition. For example, glycerine may be present in the amount of about 1 to about 5% by weight. Polyethylene glycol and triethyl citrate may be used in the amount of about 5% to about 12%, in one embodiment.

Figure 2:
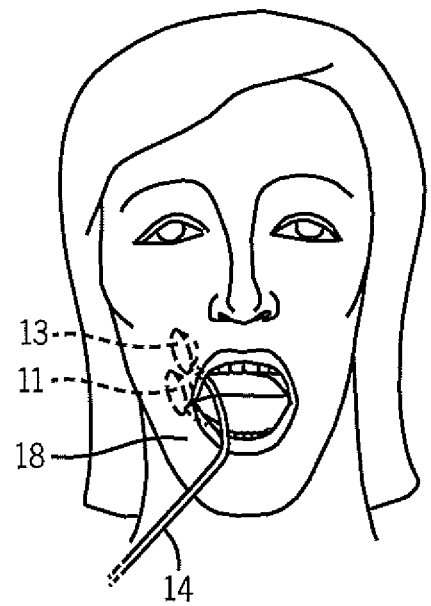
FIG. 2 illustrates a perspective view of a patient with the sensor placed on buccal tissue for evaluation of tissue impedance according to an embodiment.

FIG. 2 illustrates the sensor 10 including the electrodes 11 and 13, as placed inside the mouth of the patient 18 on the buccal tissue, according to an embodiment. The electrodes 11 and 13 may be suitably sized and shaped such that the patient 18 may easily close his or her mouth around the electrodes with minimal discomfort. The present embodiment shows two electrodes 11 and 13 that are not fixed in distance relative to one another. In this case, analysis of impedance measurements allows a variable distance between the electrodes. Such an embodiment may be appropriate for assessing changes in the electrical of the tissue over time. Once electrodes 11 and 13 are placed in the patient's mouth, impedance changes in the oral mucosa may be monitored. In such an embodiment, the collected impedance measurements may be assessed for changes that fall outside of a statistical deviation, which may signal the onset of hypoperfusion. For example, a running average of the impedance measurements may be calculated. If the running average changes at a rate faster than a predetermined threshold, an alarm may be activated.

Figure 3:
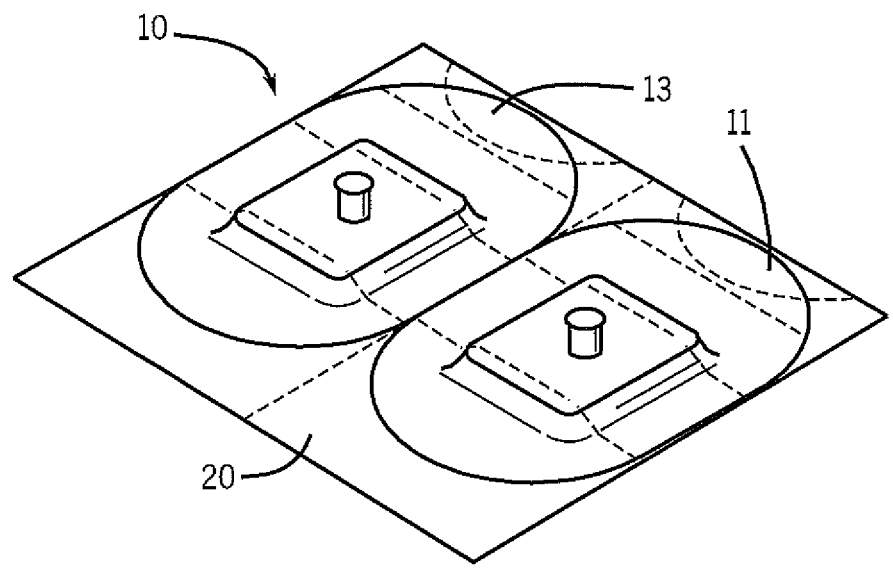
FIG. 3 illustrates a perspective view of an electrical impedance sensor with two electrodes placed on a flexible nonconducting sheet according to an embodiment.

An embodiment is shown in FIG. 3 in which electrodes 11 and 13 are capable of being placed at a predetermined, fixed distance apart on the mucosal tissue. The embodiment uses a flexible non-conducting sheet 20 to maintain fixed spacing between the electrodes. The flexible non-conducting sheet may be made of any suitable material, such as plastic, neoprene, or rubber. A mucoadhesive layer (not pictured) may be placed on the tissue contacting surface of the non-conducting sheet to adhere the sensor to the mucosal tissue. In the embodiment, the electrical impedance data may be compared to a threshold or a reference value that has been empirically determined in order to assess if the impedance measurement is within an acceptable predetermined range. The electrodes 11 and 13 may be placed on the oral mucosa at a fixed distance that correlates to the distance at which the reference data was collected. For example, the electrical impedance of the oral mucosal tissue may be assessed prior to surgery to provide a reference value, and then the impedance may be spot-checked during a surgical procedure. In another embodiment the distance between the electrodes may be measured by a monitor. In the embodiment, the impedance value would be scaled, according to the measured distance, to correlate the measured impedance value with the distance at which the reference value was collected.

Figure 4:
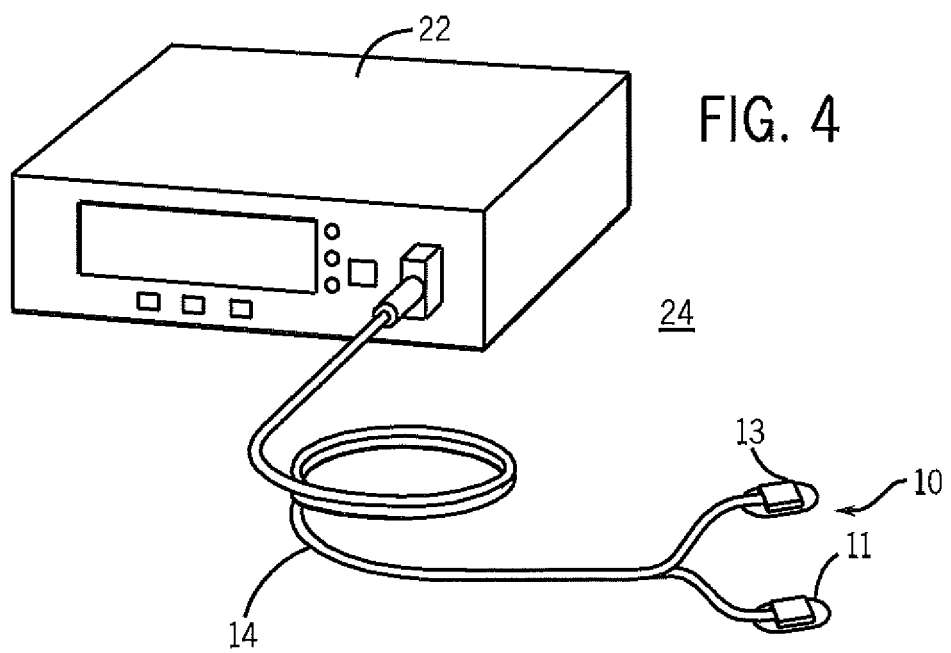
FIG. 4 illustrates a perspective view of a monitoring system according to the present disclosure according to an embodiment.
Figure 5:
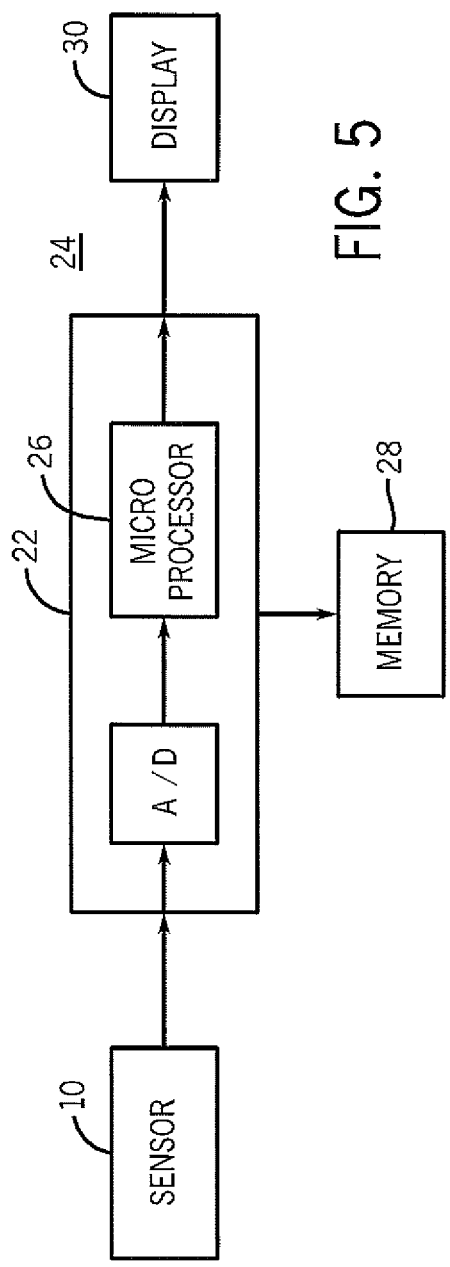
FIG. 5 a schematic view of the system of FIG. 4.

The diagram of FIG. 4 shows a monitor 22, which may be a component of an exemplary impedance monitoring system 24. The system 24 may also include a sensor 10 with a lead 14. The monitor 22 may be any suitable device for reading, recording, processing, and/or displaying the impedance measurement as well as the state of the gut tissue. A schematic view of the impedance monitoring system 24 is shown in FIG. 5. Sensor 10 may be connected to transmit an impedance measurement to monitor 22. In the present embodiment, the monitor 22 may include an analog-to-digital converter 25 as well as a microprocessor 26, which provides analysis of the measurement data. As will be appreciated by one of ordinary skill in the art, the measurement data may be stored in a memory 28 and may also be displayed on a display 30 as an alarm or by other graphical means. The display 30 may be part of the monitor 22 or it may be separate. Further, the monitor 22 may include a driver (not shown) to drive the current to the current source electrode 11.

The monitor 22 may be capable of receiving signals from the sensor 10 related to the electrical impedance of a patient's mucosal tissue. The signals sent from the sensor 10 may include a code or other identification parameter that may allow the monitor 22 to select an appropriate software instruction for processing the signal. Based on the value of the received signals corresponding to voltage drop across the electrodes 11 and 13, the microprocessor 26 may calculate the electrical impedance using various algorithms. The impedance Z may be calculated as the ratio of voltage (V) to current (I); i.e., $Z=V/I$. In addition, the memory 28 may contain comparison charts or tables for comparing measured impedance or measured impedance changes with clinically-derived impedance values that may correlate with specific disease states. In one embodiment, the processing algorithm may receive the voltage measurement and calculate a numerical indicator of the electrical impedance for display. In one embodiment, an algorithm may use as input electrical impedance data to output a more qualitative display output that correlates to a patient clinical condition.

In an embodiment, a threshold impedance value, based on reference data, may be established for the impedance measurement. As long as the measured impedance value remains well below the threshold value, the monitor 22 may illuminate a corresponding green light, indicating a "healthy" status. If the measurement value is within a predetermined range, e.g. within 5% of the threshold, then a yellow light may be illuminated, signaling a "warning" status. The "warning" range may correlate to an acceptable standard variance, as determined by statistical analysis of impedance data. Finally, if the measurement exceeds the threshold impedance, a red light may be displayed, indicating a clinical condition of gut hypoperfusion.

In an embodiment, the analysis of the impedance measurement data may include a threshold comparison to the raw data. Alternatively, the analysis may include a comparison of the threshold to a running average or mean of the measurement, to ensure that measurement errors do not result in false alarms. The aforementioned analysis may correspond to an embodiment where predetermined reference data may be used to establish a threshold impedance value. In another embodiment, the impedance data may be monitored for changes in value. In the corresponding embodiment, a threshold may be established for an alarm by a change that exceeds a certain percentage difference, as compared to a prior reading. Again, the impedance change data may use raw values, comparing successive readings, or the data may constitute a comparison of the running average to an average of prior data, to avoid false alarms.

Figure 6:
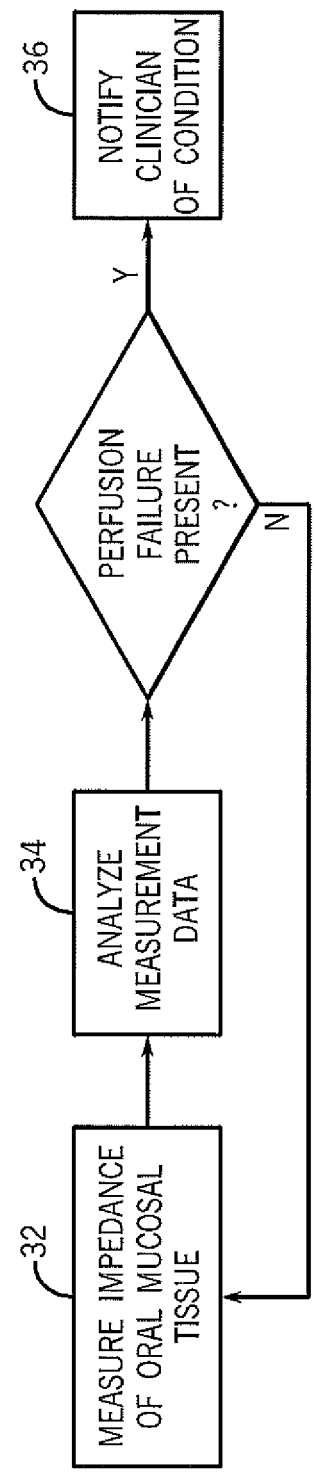
FIG. 6 illustrates a flow chart for monitoring a patient according to an embodiment.

FIG. 6 is a flow chart of an embodiment of a perfusion failure monitoring system. In the embodiment, the impedance of the oral mucosal tissue of a patient may be measured (block 32). Next, the measurement data may be analyzed to determine if perfusion failure is present by comparing the data to a threshold, for example (block 34). If perfusion failure is present, then the clinician is notified of the condition (block 36). For example, the clinician may be notified by an audible alarm and/or a flashing red light. If no perfusion failure is detected, then the impedance of the mucosal tissue may continue to be evaluated.

In one embodiment, the disclosed method of monitoring hypoperfusion in the gut may be used during a surgical procedure. In such an embodiment, a plurality of baseline measurements of the mean oral electrical impedance may be recorded, for example over a five or ten minute period prior to the surgery. These baseline measurements may then be used to compute a baseline value of mean oral electrical impedance as well as the standard variance. After the data are collected for determining the baseline value and the variance, the electrical impedance values of the oral mucosal tissue may be periodically measured between the electrode pair over the course of the surgery. The data representing these periodically measured impedance values may be compared against the stored baseline values, as shown in block 34. If the measured electrical impedance varies from the baseline and standard variance, an alarm may be triggered to alert the surgeon to possible hypoperfusion in the gut, as discussed above.

Figure 7:
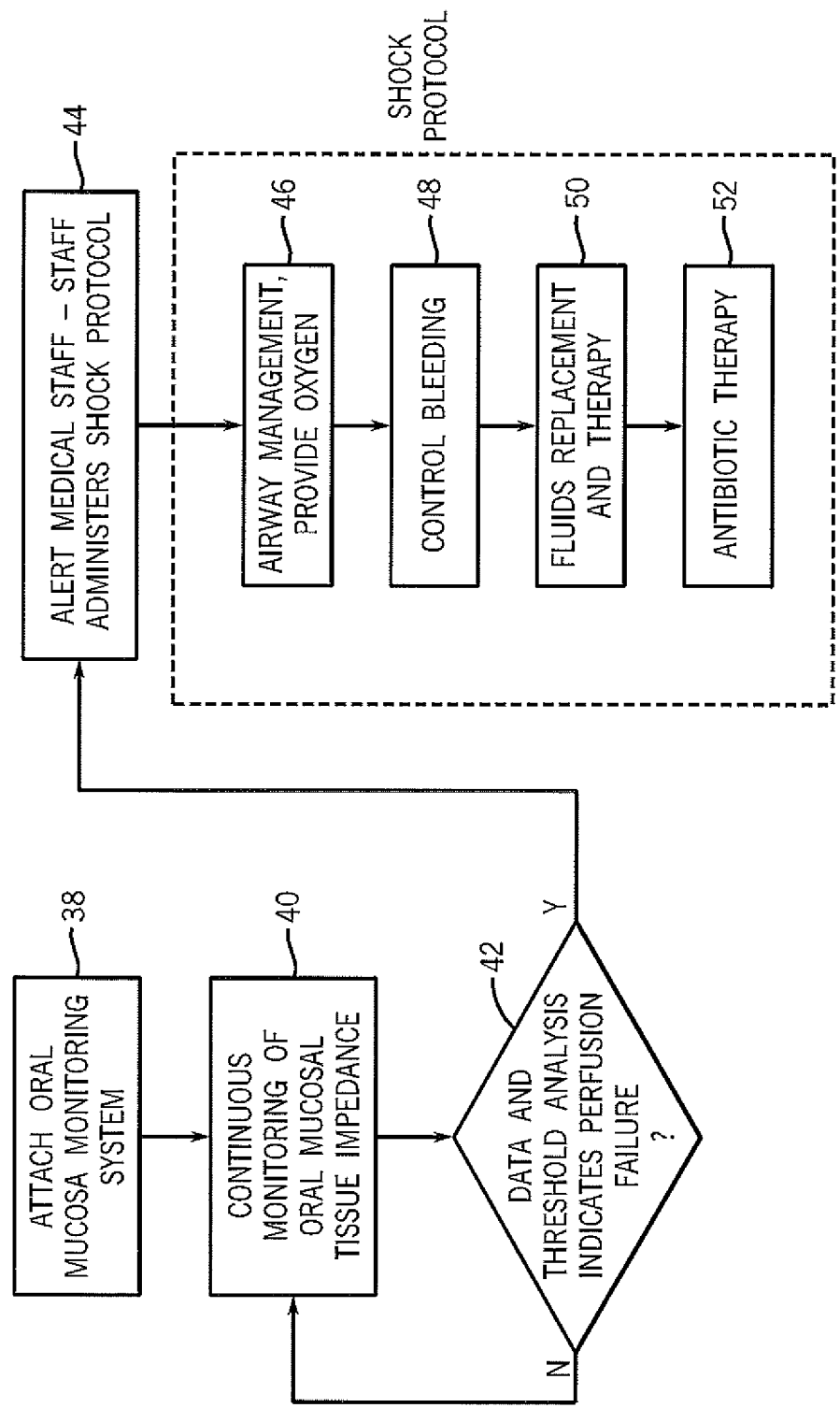
FIG. 7 illustrates a flow chart for monitoring a patient and administering a shock protocol according to an embodiment.

FIG. 7 shows a detailed example of an embodiment of the process that may lead to detection of hypoperfusion and a shock protocol that may be administered in response to the alarm. Initially, an oral mucosa monitoring system may be connected to a subject (block 38). The impedance of the oral mucosal tissue may be then continuously monitored (block 40). The impedance measurement may be analyzed as discussed above to determine the presence of perfusion failure (block 42). If no perfusion failure is detected, then the tissue continues to be monitored. If perfusion failure is detected, then medical staff may be alerted to subsequently administer a shock protocol (block 44). In the present embodiment, the first step of shock protocol may be to provide oxygen via airway management (block 46). Subsequently, efforts are made control and limit the patient's bleeding (block 48). The shock protocol may also include fluid replacement and therapy and/or antibiotic therapy (blocks 50, 52). As will be appreciated by one of ordinary skill in the art, the steps that may be performed during a shock treatment procedure may vary depending upon the stage of the patient's shock and guidelines provided by different healthcare institutions. One embodiment may include administration of Early Goal Directed Therapy (EGDT), such as the protocol described by Rivers et al in "Early goal-directed therapy in the treatment of severe sepsis and septic shock." *N Engl J Med* 2001; 345, 1368-1377, the text of which is incorporated by reference herein for all purposes.

While the disclosure may be susceptible to various modifications and alternative forms, embodiments have been shown by way of example in the drawings and have been described in detail herein. However, it should be understood that the embodiments are not intended to be limited to the particular forms disclosed. Indeed, the present disclosure may not only be applied to measurements of electrical impedance, but the disclosure may also be utilized for the measurement and/or analysis of other electrical properties of the tissue. Rather, the disclosure is to cover all modifications, equivalents, and alternatives falling within the spirit and scope of the disclosure as defined by the following appended claims. It will be appreciated by those working in the art that sensors fabricated using the present disclosure may be used in a wide variety of contexts.

What is claimed is:

1. A system, comprising:
a first electrode configured to apply a current to an oral or nasal mucosa of a patient;
a second electrode configured to detect the applied current from the mucosa and output an impedance measurement related to an electrical impedance of the oral or nasal mucosa; and
a monitor operatively coupled to the first electrode and the second electrode and configured to:
receive a first impedance measurement prior to a surgical procedure and perform an operation on the first impedance measurement to determine a baseline impedance value;
receive a second impedance measurement after or during the surgical procedure and perform the operation on the second impedance measurement to determine an impedance value;
compare the impedance value to the baseline impedance value to determine when the impedance value varies from the baseline impedance value; and
determine that a patient has a clinical condition comprising gut hypoperfusion, gut ischemia, shock, and/or organ failure when the impedance value varies from the baseline impedance value.

2. The system of claim 1, wherein the monitor is configured to determine a rate of change of the impedance value over a time period, wherein the rate of change is utilized to determine the clinical condition when the rate of change exceeds a rate of change of the baseline impedance value.

3. The system of claim 1, wherein the monitor is configured to trigger an alarm when the clinical condition is determined.

4. The system of claim 1, wherein the monitor is configured to receive a plurality of first impedance measurements during a time period prior to the surgical procedure, and wherein the plurality of first impedance measurements are used to determine a plurality of baseline impedance values.

5. The system of claim 4, wherein the plurality of baseline impedance values are used to compute a mean baseline impedance value.

6. The system of claim 5, wherein the monitor is configured to trigger an alarm when the impedance value varies from mean baseline impedance value.

7. A monitor, comprising:
a processor configured to execute instructions stored on a computer readable memory;
wherein the processor is configured to:
determine a baseline impedance value from a first impedance measurement from an oral or nasal mucosa of a patient, wherein the first impedance value is acquired before a surgical procedure;
determine an impedance value from a second impedance measurement from the oral or nasal mucosa of the patient, wherein the second impedance measurement is acquired after or during the surgical procedure;
compare the impedance value to the baseline impedance value to determine when the impedance value varies from baseline impedance value; and
determine that the patient has a clinical condition comprising gut hypoperfusion, gut ischemia, shock, and/or organ failure when the impedance value varies from the baseline impedance value.

8. The monitor of claim 7, wherein the processor is configured to determine a rate of change of the impedance value over a time period, wherein the rate of change is utilized to determine the clinical condition when the rate of change exceeds a rate of change of the baseline impedance value.

9. The monitor of claim 7, wherein the processor is configured to trigger an alarm when the impedance value varies from the baseline impedance value by more than a predetermined percentage change.

10. The monitor of claim 7, wherein the processor is configured to receive a plurality of first impedance measurements during a time period prior to the surgical procedure, and wherein the plurality of first impedance measurements are used to determine a plurality of baseline impedance values.

11. The monitor of claim 10, wherein the plurality of baseline impedance values are used to compute a mean baseline impedance value.

12. The monitor of claim 7, comprising a display configured to provide an indication of the clinical condition.

* * * * *